US012721938B2

(12) United States Patent
Noack

(10) Patent No.: US 12,721,938 B2
(45) Date of Patent: Sep. 1, 2026

(54) METHOD FOR FILLING A MEMBRANE

(71) Applicant: Fresenius Medical Care Deutschland GmbH, Bad Homburg (DE)

(72) Inventor: Joachim Noack, Bad Neustadt (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 821 days.

(21) Appl. No.: 17/424,598

(22) PCT Filed: Jan. 22, 2020

(86) PCT No.: PCT/EP2020/051487
§ 371 (c)(1),
(2) Date: Jul. 21, 2021

(87) PCT Pub. No.: WO2020/152209
PCT Pub. Date: Jul. 30, 2020

(65) Prior Publication Data
US 2022/0105252 A1 Apr. 7, 2022

(30) Foreign Application Priority Data
Jan. 22, 2019 (DE) ..................... 10 2019 101 542.1

(51) Int. Cl.
*A61M 1/36* (2006.01)
*B01D 69/08* (2006.01)

(52) U.S. Cl.
CPC .......... *A61M 1/365* (2014.02); *A61M 1/3629* (2014.02); *B01D 69/08* (2013.01);
(Continued)

(58) Field of Classification Search
CPC .......... A61M 1/365; A61M 2205/3341; A61M 2205/3355; A61M 1/3649; A61M 1/1635;
(Continued)

(56) References Cited

U.S. PATENT DOCUMENTS 4,209,391 A * 6/1980 Lipps .................. A61M 1/1639 210/647
7,186,342 B2 * 3/2007 Pirazzoli ............ A61M 1/1682 210/741
(Continued)

FOREIGN PATENT DOCUMENTS

CN 1604798 A 4/2005
CN 103635211 3/2014
(Continued)

OTHER PUBLICATIONS

Japanese Office Action.
(Continued)

*Primary Examiner* — Andrew J Mensh
*Assistant Examiner* — Quynh Dao Le
(74) *Attorney, Agent, or Firm* — Kilyk & Bowersox, P.L.L.C.

(57) ABSTRACT

A method for filling a membrane filter of a blood treatment system is provided. The blood treatment system includes at least one blood treatment machine, a membrane filter, in particular a hollow fiber membrane filter, having a first and a second chamber which are semi-permeably separated by a membrane, and at least one first partial circuit and at least one second partial circuit. The first chamber of the membrane filter is arranged in the first partial circuit and the second chamber of the membrane filter is arranged in the second partial circuit. The first chamber of the membrane filter is filled with liquid via the first partial circuit, whilst the second chamber is still filled with air, and a pump is arranged in the first partial circuit upstream of the membrane filter.

20 Claims, 3 Drawing Sheets

Figure 1:
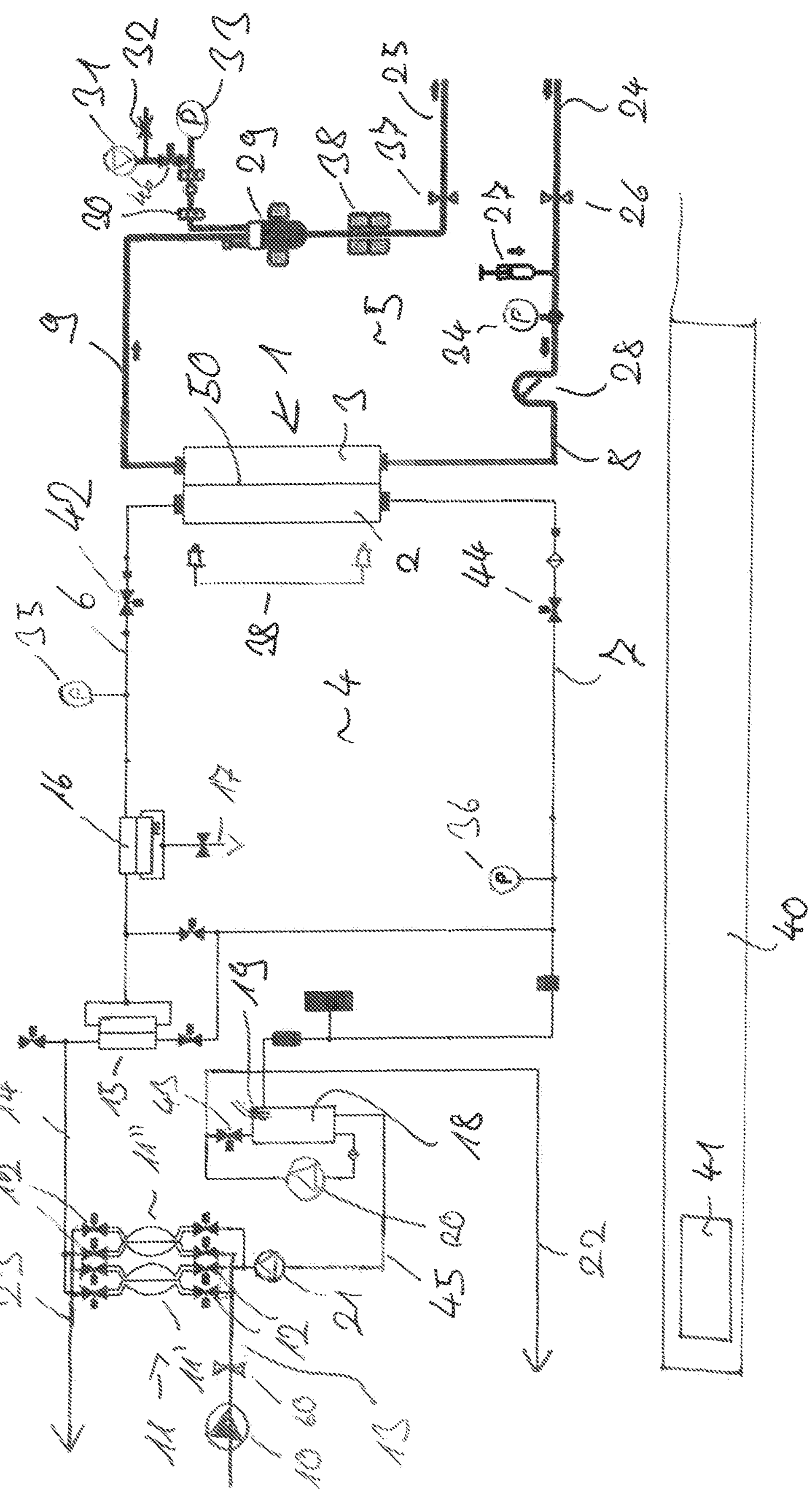

(52) U.S. Cl.
CPC ............... *A61M 2205/3341* (2013.01); *A61M 2205/3355* (2013.01)

(58) Field of Classification Search
CPC .......... A61M 2205/3331; A61M 1/288; A61M 1/3629; A61M 2005/1402; A61M 2005/1403; A61M 2205/3334; A61M 2205/3337; A61M 1/3643; A61M 1/3644; A61M 1/3646; A61M 1/3647; A61M 1/3652; A61M 1/1601–1609; A61M 1/1615; A61M 2205/3351; B01D 69/08
USPC ................................................ 604/6.09, 4.01
See application file for complete search history.

(56) References Cited

U.S. PATENT DOCUMENTS

| | | | | |
|---|---|---|---|---|
| 7,935,258 | B2* | 5/2011 | Rovatti | A61M 1/3644 210/636 |
| 2005/0230314 | A1 | 10/2005 | Kim et al. | |
| 2008/0156476 | A1* | 7/2008 | Smisson | A61M 5/44 219/541 |
| 2009/0101576 | A1* | 4/2009 | Rohde | A61M 1/3643 96/204 |
| 2009/0151470 | A1* | 6/2009 | Puppini | G01L 13/00 73/864.34 |
| 2010/0087772 | A1* | 4/2010 | Gronau | A61M 1/3646 604/6.11 |
| 2012/0298580 | A1* | 11/2012 | Gronau | A61M 1/3643 210/321.71 |
| 2012/0298590 | A1 | 11/2012 | Olsen et al. | |
| 2013/0303963 | A1* | 11/2013 | Breuch | A61M 1/3649 604/6.09 |
| 2014/0217027 | A1 | 8/2014 | Meyer et al. | |
| 2017/0143891 | A1* | 5/2017 | Bridges | A61M 1/3638 |
| 2018/0154066 | A1* | 6/2018 | Briggs | A61M 1/3609 |
| 2019/0321533 | A1 | 10/2019 | Hacker et al. | |
| 2020/0330682 | A1* | 10/2020 | Callan | A61M 5/007 |
| 2023/0256151 | A1* | 8/2023 | Wuerschmidt | A61M 1/3649 210/646 |

FOREIGN PATENT DOCUMENTS

| | | | | |
|---|---|---|---|---|
| CN | 105025951 | | 11/2015 | |
| CN | 106573099 | | 4/2017 | |
| CN | 106730086 | | 5/2017 | |
| CN | 108697990 | | 10/2018 | |
| DE | 10011208 | | 9/2001 | |
| DE | 10011208 | C1 * | 9/2001 | A61M 1/3431 |
| DE | 102011102492 | | 11/2012 | |
| DE | 102015009886 | | 2/2017 | |
| DE | 102015009886 | A1 * | 2/2017 | A61M 1/1658 |
| EP | 2583702 | A1 | 4/2013 | |
| EP | 2662101 | | 11/2013 | |
| JP | 2008-012210 | | 1/2008 | |
| JP | 2018-527976 | | 9/2018 | |
| WO | WO 2008/125893 | | 10/2008 | |
| WO | 2018130592 | A1 | 7/2018 | |
| WO | WO-2019049968 | A1 * | 3/2019 | A61M 1/3624 |

OTHER PUBLICATIONS

Search Report issued in corresponding Chinese Patent Application 202080010042.7 dated Nov. 22, 2024 (English translation only) (2 pages).
Chinese Office Action dated Aug. 30, 2024.

* cited by examiner

METHOD FOR FILLING A MEMBRANE

The present invention relates to a method of filling a membrane filter of a blood treatment system, wherein the blood treatment system has at least one membrane filter, in particular a hollow fiber membrane filter, having a first and a second chamber that are semipermeably separated by a membrane, at least one first partial circuit and at least one second partial circuit, wherein the first chamber of the membrane filter is arranged in the first partial circuit and the second chamber of the membrane filter is arranged in the second partial circuit, and wherein the filling of the first chamber of the membrane filter with liquid via the first partial circuit takes place while the second chamber is still filled with air. The present invention furthermore comprises a corresponding blood treatment machine and a blood treatment system.

A filling method is known from DE 10 2011 102 492 A1. In this process, the filling of the first chamber of the membrane filter via the first partial circuit takes place such that air is displaced from the first partial circuit into the second partial circuit at least over a partial phase of the filling.

DE 10 2015 009 886 A1 furthermore shows a method in which an excess pressure with respect to the second chamber is applied to the first chamber after the filling of the first chamber of the membrane filter via the first partial circuit.

It is furthermore known from WO 2008/125893 A1 for the filling of the first and second partial circuits to connect the venous line and the arterial line of the second partial circuit to a section of the first partial circuit disposed downstream of the membrane filter and to control pumps arranged in the first partial circuit downstream of the membrane filter and downstream of the connection points to the venous line and to the arterial line in dependence on a pressure in the first and second partial circuits. The control of a pump arranged upstream of the membrane filter takes place in a volume controlled manner in contrast.

In the sense of this description, the terms “upstream” and “downstream” mean the direction of flow the liquids flow through the lines on operation during a treatment. This can, for example, be recognized in that a blood leak detector can be arranged downstream of the membrane filter. It can be suitable to detect blood that passes through the membrane from the second partial circuit into the first partial circuit during the treatment. An air separation chamber can be arranged downstream. With respect to the partial circuit filled with blood during operation, “upstream” can designate the line section in which a blood pump and/or an addition point for heparin is/are arranged.

It is the object of the present invention to provide a method and a treatment machine that permit a reliable filling of the membrane filter.

This object is achieved by: a method of filling a membrane filter of a blood treatment system, wherein the blood treatment system has at least one blood treatment machine, a membrane filter, in particular a hollow fiber membrane filter, having a first and a second chamber that are semipermeably separated by a membrane, and at least one first partial circuit and at least one second partial circuit, wherein the first chamber of the membrane filter is arranged in the first partial circuit and the second chamber of the membrane filter is arranged in the second partial circuit, wherein the filling of the first chamber of the membrane filter with liquid via the first partial circuit takes place while the second chamber is still filled with air, wherein the first partial circuit is preferably a dialyzate circuit and/or the second partial circuit is an extracorporeal blood circuit, and wherein a pump is arranged upstream of the membrane filter in the first partial circuit, characterized in that the control of the pump for filling the first chamber of the membrane filter takes place via the first partial circuit in dependence on a measured pressure in the first partial circuit and on a measured pressure in the second partial circuit; and by a treatment machine to which at least one membrane filter, in particular a hollow fiber membrane filter, can be coupled, having a first chamber and a second chamber that are semipermeably separated by a membrane, said blood treatment machine comprising: at least one first pump actuator of a first pump for pumping liquid in a first partial circuit and at least one second pump actuator of a second pump for pumping liquid in a second partial circuit, wherein the first chamber of the membrane filter is arranged in the first partial circuit and the second chamber of the membrane filter is arranged in the second partial circuit, with the first pump being arranged upstream of the membrane filter in the first partial circuit; at least two pressure sensors for measuring a pressure in the first partial circuit and in the second partial circuit; and a control that evaluates the signals of the pressure sensors and controls actuators of the blood treatment machine, characterized in that the control comprises a filling program that carries out a control of the first pump actuator for filling the first chamber of the membrane filter via the first partial circuit in dependence on the pressures measured in the first and second partial circuits.

Embodiments of the present invention form the subject of the dependent claims. The present invention comprises a method of filling a membrane filter of a blood treatment system, wherein the blood treatment system has at least one blood treatment machine, a membrane filter, in particular a hollow fiber membrane filter, having a first and a second chamber that are semipermeably separated by a membrane, at least one first partial circuit and at least one second partial circuit, wherein the first chamber of the membrane filter is arranged in the first partial circuit and the second chamber of the membrane filter is arranged in the second partial circuit, wherein the filling of the first chamber of the membrane filter with liquid via the first partial circuit takes place while the second chamber is still filled with air, and wherein a pump is arranged upstream of the membrane filter in the first partial circuit. The method is characterized in that the control of the pump for filling the first chamber of the membrane filter via the first partial circuit takes place in dependence on a pressure measured in the first and second partial circuits.

An even more reliable filling of the membrane filter is made possible by the control of the pump in dependence on the pressure. The remaining of air islands within the membrane filter can thus be further reduced in some embodiments. The filling state can be detected in some embodiments.

In a preferred embodiment, the first partial circuit is the dialyzate circuit and/or the second partial circuit is an extracorporeal blood circuit. The present invention therefore in particular relates to the filling of the dialyzate chamber of a dialyzer.

In a possible embodiment of the present invention, air present in the first chamber during the filling of the first chamber of the membrane filter with liquid is displaced via the membrane into the second chamber of the membrane filter and thus into the second partial circuit.

In a possible embodiment of the present invention, the filling of the first chamber of the membrane filter takes place from top to bottom via the first partial circuit. The filling of the first chamber of the membrane filter via the first partial circuit preferably takes place with the same direction of flow by which the membrane filter is also flowed through during the blood treatment.

In a preferred embodiment, the filling of the two chambers of the membrane filter takes place without an interposed rotation of the membrane filter.

In a possible embodiment of the present invention, the membrane filter is operated in a counterflow in the first and second partial circuits during the blood treatment. If therefore the first chamber of the membrane filter is filled from top to bottom via the first partial circuit, in particular in the dialyzate circuit, the second chamber of the membrane filter can be filled and/or flushed from bottom to top via the second partial circuit, in particular in the blood circuit, with the same direction of flow used during the blood treatment without rotating the membrane filter. A secure venting of the second chamber of the membrane filter can hereby be achieved.

In a possible embodiment of the present invention, the volume flow generated by the pump and used for filling and/or the time development and/or the duration of the filling by the pump is controlled in dependence on a pressure measured in the first and/or second partial circuit(s).

In accordance with a first variant of the present invention, a pressure in the first partial circuit is measured and/or a transmembrane pressure over the membrane of the membrane filter is measured, with the control of the pump for filling the first chamber of the membrane filter via the first partial circuit taking place in dependence on the pressure in the first partial circuit and/or on the transmembrane pressure. The pressure can in particular be measured upstream and/or downstream of the first chamber in the first partial circuit and the filling of the first chamber of the membrane filter via the first partial circuit can take place in dependence on this pressure.

The determination of the transmembrane pressure can take place using a pressure, measured by means of a pressure sensor at the second partial circuit, and using a pressure, measured by means of a further pressure sensor at the first partial circuit. The transmembrane pressure can be determined by means of these two pressure values and a third pressure value, measured by means of a third pressure sensor at the first partial circuit, with the further pressure senor being able to be arranged upstream of the membrane filter and the third pressure sensor being able to be arranged downstream of the membrane filter. The determination can take place in that the mean value of the pressures measured by means of the further pressure sensor and of the third pressure sensor is formed and that the pressure in the second partial circuit is deducted thereat or the mean value can be deducted at the pressure in the second partial circuit.

The present invention in accordance with this first variant is based on the recognition that some membrane filters, in particular some dialyzers, are very sensitive with respect to the pressure over the membrane as long as the second chamber is still not filled with liquid. If a certain transmembrane pressure is applied to the membrane filter over a certain time period in this situation, liquid will pass from the first chamber, in particular the dialyzate chamber, into the second chamber, in particular the blood chamber, and the latter can later no longer be properly filled. It must be considered here that where liquid has filled the capillaries in the dialyzer, air can no longer pass through the capillaries of the fiber wall. Conversely, a certain transmembrane pressure is, however, required to effectively displace the air from the first chamber over the membrane into the second chamber.

Since the transmembrane pressure is decisively determined by the pressure in the first partial circuit and in particular by the pressure upstream of the first chamber, the pressure in the first partial circuit and in particular the pressure upstream of the first chamber can be measured alternatively to the transmembrane pressure and can be used or restricted for the control.

In a possible embodiment, the filling is controlled such that the pressure in the first partial circuit and/or the transmembrane pressure does/do not exceed a first threshold value.

A delivery rate of the filling is preferably reduced as soon as the pressure in the first partial circuit and/or the transmembrane pressure exceeds/exceed a first threshold value. The reduction of the filling can also comprise a complete stop of the filling. A liquid inflow can in particular be reduced and in particular stopped for so long until the pressure in the first partial circuit and/or the transmembrane pressure is/are again below the first threshold value or a second threshold value.

In a possible embodiment, a delivery rate of the pump during the filling is reduced or the pump is stopped as soon as the pressure in the first partial circuit and/or the transmembrane pressure exceeds/exceed a first threshold value, with the first threshold value amounting to at least 50 mbar, for example; at least 100 mbar, for example; or at least 200 mbar, for example.

In a possible embodiment, a delivery rate of the pump during the filling is increased or the pump is started again as soon as the pressure in the first partial circuit and/or the transmembrane pressure falls/fall below a second threshold value, with the second threshold value amounting to at least 50 mbar, for example; at least 100 mbar, for example; or at least 150 mbar, for example.

An absolute value of the first threshold value is preferably greater than an absolute value of the second threshold value. If the two threshold values are of equal amounts, this could have the result that the pump would constantly start and stop. This is prevented by different threshold values.

In a possible embodiment, the pump is controlled such that an excess pressure arises at least at times in the first chamber of the membrane filter, in particular a pressure of at least 50 mbar, for example; or at least 100 mbar, for example; or at least 200 mbar, for example.

In a possible embodiment, the pump is controlled in a volume-controlled manner for the filling of the first chamber of the membrane filter, with the volume-controlled control being stopped or with the volume flow being reduced as soon as the pressure in the first partial circuit and/or the transmembrane pressure exceeds/exceed a first threshold value, with the first threshold value amounting to at least 50 mbar, for example; at least 100 mbar, for example; or at least 200 mbar, for example.

In a possible embodiment, the volume-controlled control is restarted or the volume flow is increased as soon as the pressure in the first partial circuit and/or the transmembrane pressure exceeds/exceed a second threshold value, with the second threshold value amounting to at least 50 mbar, for example; or at least 100 mbar, for example; or at least 150 mbar, for example.

An absolute value of the first threshold value is preferably greater than an absolute value of the second threshold value.

It can be ensured by the pressure limitation or flow limitation in accordance with the invention that no air cushions are included in the fiber bundle of the membrane filter than can subsequently no longer be separated. The control in accordance with the invention, however, further ensures that a sufficient pressure is applied at the first chamber to displace air located there over the membrane into the second chamber.

In a possible embodiment, the first chamber of the membrane filter is filled with a pulsatile volume flow by which pressure peaks are produced in the first chamber of the membrane filter. The pressure peaks and the respective subsequent pressure drop are here produced in the rhythm of the pulsatile volume flow.

The pump preferably cooperates with a balancing chamber assembly that has liquid applied to it by the pump and whose switchovers result in a pulsatile volume flow.

In a possible embodiment, no liquid is drained from the system at least at times during the filling of the first chamber of the membrane filter. This enables a faster filling of the first partial circuit.

A fluid communication of a secondary air separator arranged downstream of the first chamber in the first partial circuit with the drain can in particular be closed during the filling and/or a pump arranged there cannot be operated. This can in particular take place during the pressure-controlled filling, in particular during the total pressure-controlled filling.

In a possible embodiment, a pump arranged downstream of the membrane filter in the dialyzate circuit is not operated at least at times during the filling of the first chamber of the membrane filter. A pump arranged downstream of the membrane filter in the first dialyzate partial circuit can in particular not be operated at least at times. The pump or pumps can in particular be arranged downstream of a secondary air separator arranged in the first partial circuit. The pump or pumps is/are preferably not operated during the total pressure-controlled filling.

In a further variant, the pressure in the second partial circuit is measured, with the filling of the first chamber of the membrane filter via the first partial circuit taking place and with the control of the pump in particular taking place in dependence on the pressure in the second partial circuit.

The measurement of the pressure in the second partial circuit can here, in a first embodiment of the present invention, be part of a measurement of the transmembrane pressure as has already been described above.

Alternatively or additionally, the filling of the first chamber of the membrane filter via the first partial circuit can also take place in dependence on the absolute pressure and/or on pressure changes in the second partial circuit.

The process management is based on the recognition that the filling level of the first chamber of the membrane filter can be determined by measurement of the pressure in the second partial circuit. The present invention here in particular makes use of the fact that on a passage of air from the first chamber through the membrane into the second partial circuit, the pressure in the second partial circuit increases.

If the second partial circuit is open to the atmosphere, dynamic pressure changes are produced by the nevertheless present flow resistance. If the second partial circuit is closed to the atmosphere, static pressure changes are also produced.

Dynamic and/or static pressure changes in the second partial circuit can therefore in particular be detected and/or monitored.

In a possible embodiment of the present invention, the pressure in the second partial circuit is monitored with respect to pressure changers, in particular pressure fluctuations. The time sequence of the filling of the first chamber here preferably depends on a detection of pressure changes in particular pressure fluctuations, and in particular on a point in time at which pressure changes, in particular pressure fluctuations, are detected and/or are no longer detected.

In a possible embodiment of the present invention, a complete filling of the first chamber of the membrane filter is recognized by the monitoring for pressure changes, in particular pressure fluctuations, with a conclusion on a complete filling preferably being made when pressure changes, in particular pressure fluctuations, are no longer detected.

In a possible embodiment of the present invention, the filling of the first chamber is continued for so long as pressure changes, in particular pressure fluctuations, are detected in the second partial circuit. A minimum residual filling phase can furthermore still be carried out once pressure changes, in particular pressure fluctuations, are no longer detected.

In a possible embodiment of the present invention, the filling of the first chamber is continued for so long as air is detected in a secondary air separator of the first partial circuit, with a minimum residual filling phase preferably still being carried out once air is no longer detected.

If the membrane is therefore already not air-permeable from the start due to the material used or if it was already completely soaked before the air had been completely displaced from the first chamber of the membrane filter, the air is displaced on a (further) filling of the first chamber of the membrane filter via the first partial circuit into the secondary air separator arranged downstream of the membrane filter in the first partial circuit. It can therefore be ensured by the monitoring of the secondary air separator that air is no longer pumped from the first chamber of the first membrane filter into the first partial circuit and a complete filling is therefore also present with this constellation.

It is ensured by the monitoring of the pressure in the second partial circuit and/or of the air in the secondary air separator that the membrane is completely wetted at the end of this step, that is, the dialyzer is best possibly filled in an embodiment without rotation.

The minimum residual filling phase then serves as a safety buffer and for flushing the membrane filter. It can have a constant length.

The minimum residual filling phase can comprise a predefined pump volume, a predefined time, or a predefined number of pump beats and/or balancing chamber switchovers.

The filling of the first chamber of the membrane filter via the first partial circuit preferably takes place with a pulsatile volume flow. The pulsatile volume flow can be generated by means of a membrane pump, for example in the form of a balancing chamber. The filling can in particular take place over a plurality of balancing chamber switchovers. The filling can, however, also takes place with a constant volume flow.

In a possible embodiment of the present invention, the first partial circuit is filled at least during a starting phase of the filling of the first chamber with a first volume flow of a maximum of 800 ml/mm, preferably of a maximum of 500 ml/min. This limitation can be present here independently of the pressure measured. After the starting phase, it is possible to work with a larger maximum volume flow, with the volume flow being able to be controlled in dependence on a measured pressure.

In a possible embodiment of the present invention, the second partial circuit is open to the atmosphere, i.e. it is in fluid communication with the atmosphere, during the filling of the first chamber of the membrane filter via the first partial circuit. The counter-pressure produced by the air in the second partial circuit is hereby reduced and/or vented.

In a possible embodiment of the present invention, the second partial circuit is in fluid communication with the atmosphere during the filling of the first chamber of the membrane filter via an element that generates a pressure drop. The connection to the atmosphere preferably takes place via a filter, in particular a hydrophobic filter and/or sterile filter and/or a restrictor and/or a valve. A certain resistance hereby remains to the filling of the second partial circuit with the air from the first chamber via the membrane, which results in pressure changes due to the filling process.

In a possible embodiment of the present invention, liquid and/or air is displaced from the first chamber into a secondary air separator that is arranged in the first partial circuit downstream of the membrane filter during the filling of the first chamber of the membrane filter via the first partial circuit. The filling of the first chamber and the removal of air from the first chamber is hereby improved.

In a possible embodiment, the secondary air separator is not connected to a liquid drain of the system, at least at time, in particular in that the corresponding fluid connection is closed or a pump is not operated. Liquid hereby does not flow out of the system so that the filling is accelerated.

In a possible embodiment of the present invention, the secondary air separator that is arranged in the first partial circuit downstream of the membrane filter is not connected to the atmosphere, at least at time, during the filling of the first chamber of the membrane filter via the first partial circuit. Depending on the design of the fluid circuits, this can have the result of a faster increase of the transmembrane pressure to a desired value and thus of a greater volume flow through the membrane.

A connection to the atmosphere is, for example, only established during the total pressure-controlled filling when air is detected in the secondary air separator.

The secondary air separator can have a vessel having an inflow and an outflow, preferably in the lower region, for example in the bottom or in the lower third of the vessel, so that air collects in the upper region of the vessel and effects a dropping of the liquid level in the vessel.

The falling or rising of the level can be recognizable by the control of the blood treatment apparatus by means of a level sensor.

In a possible alternative embodiment of the present invention, a secondary air separator that is arranged in the first partial circuit downstream of the membrane filter is continuously connected to the atmosphere during the filling of the first chamber of the membrane filter via the first partial circuit. Air can hereby also be displaced in the direction of the atmosphere by the first partial circuit. The connection to the atmosphere can be present by an opening in the upper region of the vessel of the secondary air separator.

In a possible embodiment of the present invention, the first partial circuit is not filled in a balancing manner, at least at times, during the pressure-controlled filling.

Non-balancing filling has the meaning here that it is not the same liquid volume that is supplied to and removed from the partial circuit. As a result liquid is thereby supplied to the first partial circuit in total. On a balancing filling, the same liquid volume is supplied to and removed from the first partial circuit. There is thereby above all a displacement of the liquid in the first partial circuit and with this displacement of the liquid there is also a displacement of air that can then be separated in the secondary air separator.

In a possible embodiment of the present invention, the filling of the first chamber of the membrane filter via the first partial circuit starts without a balancing phase. Alternatively or additionally, the filling of the first chamber of the membrane filter via the first partial circuit takes place in a non-balancing manner at least up to a detection of a filling. The detection of the filling can take place, for example, with reference to the level sensor of the secondary air separator.

In a possible embodiment of the present invention, the filling of the first chamber of the membrane filter via the first partial circuit takes place with a balancing phase, in contrast, which is followed by a non-balancing phase. In the balancing phase, the air from the first chamber is preferably displaced into a secondary air separator arranged downstream of the membrane filter in the first partial circuit.

The filling of the first chamber of the membrane filter is preferably preceded by a filling of the first partial circuit. The filling of the first chamber of the membrane filter therefore preferably starts from a situation in which the first partial circuit is otherwise already filled.

The first partial circuit can in particular be filled in a first step and the filling of the first chamber of the membrane filter can only take place in a second step. The membrane filter can be separated from the first partial circuit for the first step and can only be fluidically connected to the first partial circuit for the second step.

The first partial circuit is preferably filled in a first step without the first chamber of the membrane filter being fluidically connected to the first partial circuit and the first chamber of the membrane filter is fluidically connected to the first partial circuit in a second step to fill said first chamber.

The membrane filter can be separated from the first partial circuit via valves for the first step and/or can be bridged by a bypass line. The valves are opened and/or the bypass line is closed after the filling of the first partial circuit.

The first step can take place without a membrane filter arranged at the blood treatment apparatus; it can, for example, take place at the end of a preceding treatment, for example to flush the first partial circuit. In the then following treatment, the first partial circuit is then initially already filled with the exception of the membrane filter.

Alternatively, a short-circuit piece can be inserted into the first partial circuit instead of the membrane filter for the first step or its ends can be directly connected to one another. The short-circuit piece is then replaced with the dialyzer for the second step and/or the dialyzer is inserted into the first partial circuit.

The present invention further comprises a blood treatment machine to which at least one membrane filter, in particular a hollow fiber membrane filter, can be coupled that has a first and a second chamber that are semipermeably separated by a membrane, said blood treatment machine comprising:

- at least one first pump actuator of a first pump for pumping liquid in a first partial circuit and at least one second pump actuator for pumping liquid in a second partial circuit, wherein the first chamber of the membrane filter is arranged in the first partial circuit and the second chamber of the membrane filter is arranged in the second partial circuit, with the first pump being arranged upstream of the membrane filter in the first partial circuit;
- at least two pressure sensors for measuring a pressure in the first partial circuit and a pressure in the second partial circuit; and
- a control that evaluates the signals of the pressure sensor and controls actuators of the blood treatment machine.

The blood treatment machine is characterized in that the control comprises a filling program that carries out a control of the first pump actuator for filling the first chamber of the membrane filter via the first partial circuit in dependence on the pressure measured in the first and second partial circuits. The same advantages hereby result that have already been described in more detail above with respect to the method in accordance with the invention.

The membrane filter is preferably a disposable that is coupled to the blood treatment machine for carrying out a treatment. The second partial circuit is preferably likewise a disposable.

In dependence on the design of the blood treatment machine, the first partial circuit can be a disposable or a fixed element of the blood treatment machine.

In a possible embodiment of the present invention, the control for carrying out the filling program controls one or more pump actuators and/or one or more valve actuators that actuate valves of the first and/or second partial circuit(s).

In a possible embodiment of the present invention, the working through of the filling program takes place automatically by the control.

In a possible embodiment of the present invention, the control is programmed to carry out a method such as was described in more detail above.

The blood treatment machine in accordance with the invention can in particular be a dialysis machine, in particular for hemodialysis and/or for hemofiltration and/or for hemodiafiltration.

The present invention further comprises a blood treatment system composed of a blood treatment machine such as was described above and of a membrane filter. The blood treatment system preferably further comprises the first and/or second partial circuit(s).

The present invention will now be described in more detail with reference to embodiments and to Figures.

Figure 2:
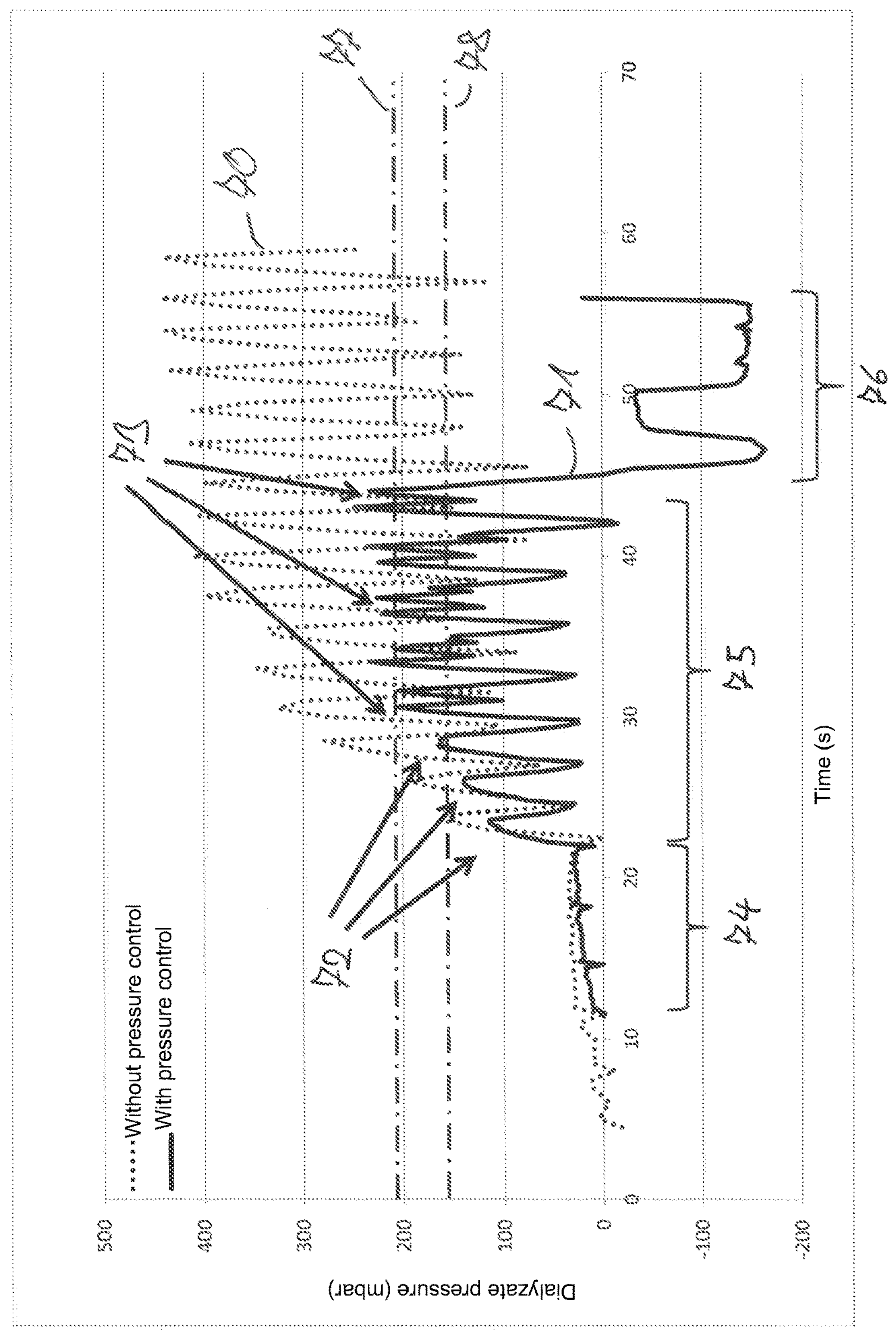
Figure 3:
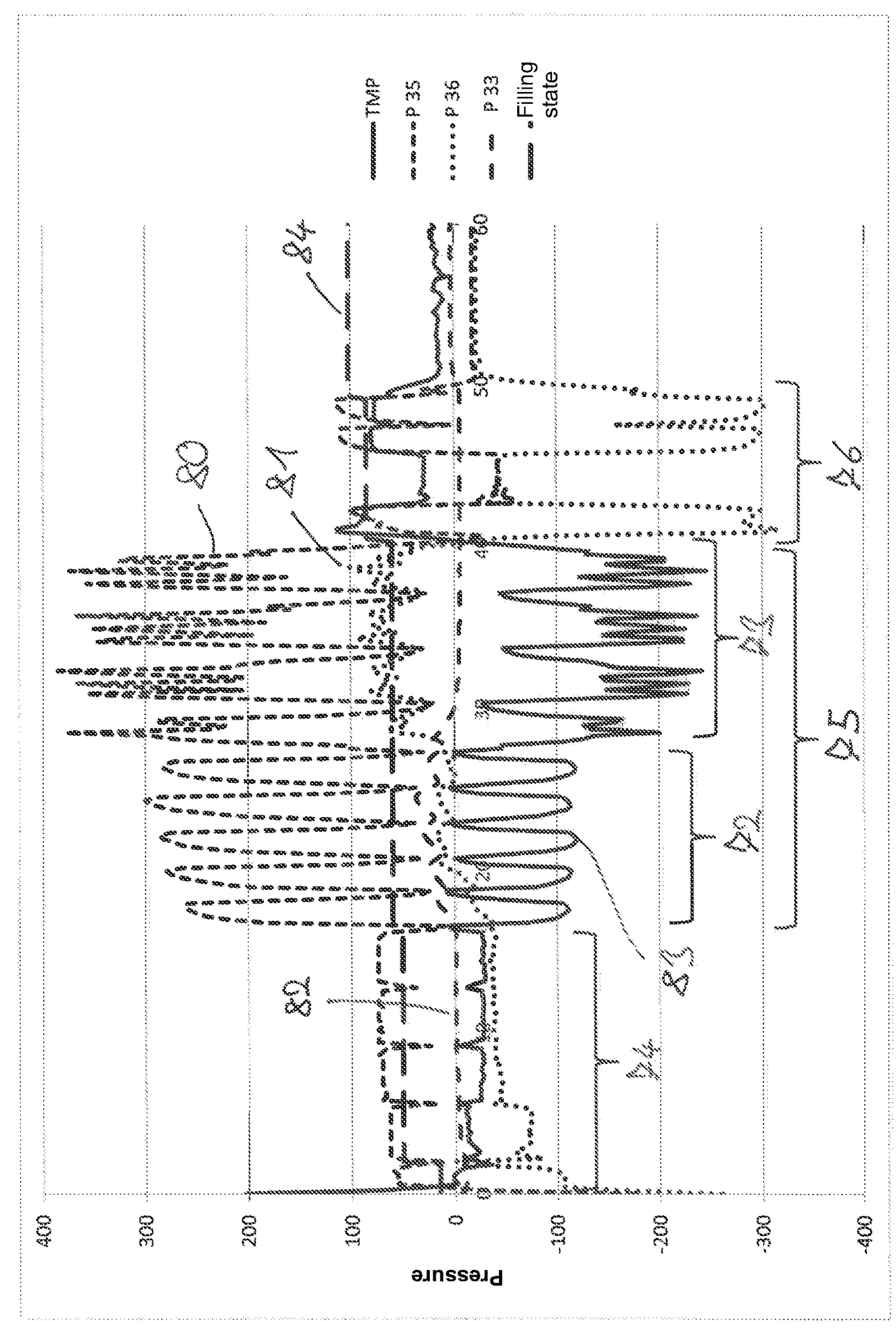

There are shown:

FIG. 1: a schematic, simplified representation of the fluid circuits of an embodiment of a blood treatment system in accordance with the invention;

FIG. 2: a diagram in which the progression of the trans-membrane pressure during the filling of the first chamber is shown for a method in accordance with the prior art and for a method in accordance with the present invention; and FIG. 3: a diagram in which the progression of the pressures measured by the individual pressure sensors of the blood treatment system during the filling of the first chamber in a method in accordance with the present invention is shown.

FIG. 1 shows a schematic, simplified representation of the fluid circuits of an embodiment of a blood treatment system in accordance with the invention. In this respect, at least those of the components of the blood treatment system that are typically present are shown that can contribute to the carrying out of the present invention. However, not all the components shown and described are also absolutely necessary for the carrying out of the invention. This results from the description on the function of the individual components.

The blood treatment system comprises a membrane filter 1. The membrane filter 1 comprises a first chamber 2 and a second chamber 3 that are semipermeably separated by a membrane 50.

The blood treatment system further comprises a first partial circuit 4 and a second partial circuit 5. The first chamber 2 of the membrane filter 1 is here arranged in the first partial circuit 4 and the second chamber 3 is arranged in the second partial circuit 5. The first chamber 2 of the membrane filter 1 is in communication with an inflow line 6 at the inlet side and with an outflow line 7 of the first partial circuit at the outlet side.

In the embodiment, the membrane filter 1 is a hollow fiber membrane filter that is configured as a dialysis filter. The first partial circuit 4 is here the dialyzate circuit and the second partial circuit 5 is the extracorporeal blood circuit.

The blood treatment system further comprises a blood treatment machine 40 that is only shown schematically here and that comprises at least one first pump actuator of a first pump 10 for pumping liquid in the first partial circuit 4 and at least one second pump actuator of a pump 28 for pumping liquid in the second partial circuit 5. The first pump 10 is here arranged upstream of the membrane filter 1 in the dialyzate circuit.

A third pump actuator of a third pump 21 and a fourth pump actuator of a fourth pump 20 are furthermore provided for pumping liquid in the first partial circuit 4 and are both arranged downstream of a secondary air separator 18 in the dialyzate circuit.

Pressure sensors 35, 36 for measuring a pressure in the first partial circuit and pressure sensors 34, 33 for measuring the pressure in the second partial circuit are further provided. The blood treatment machine 40 has a control 41 that is likewise only shown schematically, that evaluates the signals of the pressure sensor 33, 36, and that controls the actuators of the blood treatment machine.

The membrane filter 1 and the second partial circuit are preferably designed as disposables and can be coupled to the dialysis machine for carrying out a treatment. The first partial circuit can likewise be designed as a disposable in dependence on the embodiment of the system or can form a part of the blood treatment machine 40 at least in part or in full.

Preferred features of the blood treatment system will be described in more detail in the following. The present invention can, however, also be implemented with differently structured blood treatment systems.

In the embodiment, the first pump 10 in the first partial circuit 4 forms a charging pump that pumps a liquid, a dialyzate in the embodiment, via the line 13 to a balancing chamber assembly 11. The liquid flows from the balancing chamber assembly 11 via the line 14, 6 to the inlet of the first chamber 2.

A sterile filter 15 is provided in the line 14, 6 in the embodiment. A further sterile filter 16 that forms a second filter stage for the substituate line 17 is furthermore arranged downstream of the sterile filter 15.

A valve 42 via which the inflow to the membrane filter 1 can be controlled is arranged upstream of the first chamber 2 in the inflow line 6. A further valve 44 is furthermore provided downstream of the first chamber 2 in the outflow line 7.

The outlet of the first chamber 2 is connected to a secondary air separator 18 via the outflow line 7. The secondary air separator has a sensor 19 via which air can be recognized in the secondary air separator.

An outflow line 45 of the air separator 18 is connected to the balancing chamber assembly 11 via the third pump 21 configured as a dialyzate pump. Consumed dialyzate is pumped via the dialyzate pump 21 and the balancing chamber assembly 11 into the outflow line 23.

An ultrafiltration pump 20 that pumps dialyzate from the air separator 18 directly to an outflow line 22 while bypassing the balancing chamber assembly 11 is furthermore provided as a fourth pump.

The secondary air separator 18 in the embodiment furthermore has a venting valve 43 in the embodiment that connects the air separator 18 to the outflow line 22.

The second partial circuit in the embodiment has an inflow line 8 that is connected to an inlet of the second chamber 3 of the membrane filter 1 as well as an outflow line 9 that is connected to the outlet of the second chamber 3.

In the embodiment, the inflow line 8 is part of the arterial line of the extracorporeal blood circuit 5 and the outflow line 9 is part of the venous line of the extracorporeal blood circuit. The arterial line comprises a connector 24 at the patient side, an arterial clamp 26, a heparin pump 27, and a pump hose section 27, as well as a pump hose section that can be placed into a roller pump 28. The venous line has a bubble trap 29, a bubble detector 38, a venous clamp 37, and a connector 25 at the patient side.

A pressure sensor 33 is arranged at the venous bubble trap 29 via a filter 30, for example a hydrophobic filter and/or a sterile filter. The bubble trap is furthermore connected to the atmosphere via the filter 30 and the restrictor 32, with this connection being able to be opened and closed by a valve 46. An air pump 31 is furthermore provided by which an integrity test of the membrane 50 can be carried out.

Pressure sensors 35 and 36 are provided in the embodiment via which the pressure can be measured upstream and downstream of the first chamber of the membrane filter 1 in the first partial circuit 4. A pressure sensor 33 is furthermore provided to measure the pressure in the venous line of the second partial circuit and a pressure sensor 34 is provided that measures the arterial pressure upstream of the occluding roller pump 28.

Dialyzate is moved in a balancing manner in the first partial circuit 4 during the blood treatment due to the effect of the charging pump 10, the dialyzate pup 21, and the balancing chamber assembly 11. The dialyzate flows here from the balancing chamber assembly 11 via the sterile filter 15 to the first chamber 2 of the membrane filter 1 and from there onward via the secondary air separator 19 and the dialyzate pump 21 to the balancing chamber assembly 11. In the second partial circuit 5, the blood is pumped from the arterial connector 24 via the blood pump 28 to the second chamber, flows through it in counterflow to the dialyzate and flows via the bubble trap 29 to the venous connector 25.

Before the start of the treatment, the first partial circuit 4, the second partial circuit 5, and the membrane filter 1 have to be filled and optionally flushed.

An embodiment of the filling method in accordance with the invention will be described in more detail in the following.

In the embodiment, the first partial circuit 4 is first filled with liquid prior to the filling of the membrane filter. A short-circuit piece 38 is inserted into the first partial circuit for this purpose instead of the membrane filter 1 between the inflow line 6 and the outflow line 7 of the first partial circuit 4. The filling of the first partial circuit 4 with liquid takes place, for example, by actuating the charging pump 10 for filling a balancing chamber of the balancing chamber assembly with fresh dialyzate that is, for example, displaced from this balancing chamber into the line 14 by displacement of liquid that is pumped by means of the dialyzate pump 21. Alternatively, liquid can also be displaced by means of the charging pump 10 from the balancing chamber half of the first balancing chamber 11 not fluidically connected to the pump by a valve position into the second balancing chamber half of the second balancing chamber 11' not fluidically connected and liquid can be moved from the further balancing chamber half of the second balancing chamber 11' into the line 14.

After the filling of the first partial circuit, the first still unfilled membrane filter 1 is inserted into the first partial circuit instead of the short-circuit piece 38. The second partial circuit 5 is likewise connected to the membrane filter 5 and like this is not yet filled with liquid.

In accordance with the present invention, a pressure-controlled control of the first pump 10 now takes place for filling the first chamber 2 of the membrane filter 1 with liquid via the first partial circuit 4. The pressure is here measured in the first and/or second partial circuit(s) and the filling is controlled in dependence on the measured pressure. The control of the filling preferably takes place by a filling program of the control 41 of the blood treatment machine.

The central feature of the procedure in accordance with the invention or of the control in accordance with the invention is therefore a pressure-controlled filling program to control the first pump 10, said filling program being intended to avoid air inclusions in the membrane filter.

If a control, starting and/or stopping of the pump 10 is named in this description, it also covers the fact that the pump itself admittedly continues to convey, but a transport of the liquid is influenced, in particular released and/or stopped by opening or closing one or more valves, for example the vales of the balancing chambers.

The filling program preferably controls the filling in dependence on the transmembrane pressure over the membrane 50 of the membrane filter 1.

The pressure-controlled filling is preferably continued as long as a change of the venous pressure, and in particular pressure fluctuations, is observed via the pressure sensor 33.

As an optional further condition that has to be met to end the pressure-controlled filling, a demand can be made that air is no longer detected at the secondary air separator.

A minimum residual filling phase can follow this.

Features of a preferred embodiment of the filling program and of the method in accordance with the invention will be described in the following:

In the pressure-controlled filling program, the blood treatment machine preferably makes filling switchovers, i.e. the charging pump 10 conveys liquid in the first partial circuit 4 in the direction of the membrane filter 1.

For this purpose, the balancing chamber assembly 11 has two balancing chambers 11' and 11" that are switched via the associated valves 12 for the filling switchovers such that no balancing operation is present, but that the one balancing chamber rather drives the other.

The flow can be limited up to a first, low flow rate up to a predefined switchover, up to the 6th switchover after the connecting of the membrane filter 1 in the embodiment. This is, for example, 500 ml/min in the embodiment. After the predefined switchover, the filling pump 10 can work at a second, higher flow rate, in contrast. This is preferably more than 1000 ml/min, for example 1200 ml/min.

The charging pump 10 can work in a volume-controlled manner here.

If the pressure over the membrane 50, however, exceeds a first threshold value during this filling procedure, the switchover is interrupted and/or the flow rate is reduced until the pressure over the membrane has again dropped below a second threshold value. The second threshold value is preferably lower than the first threshold value to avoid too frequent a switching.

For example, the switchover can be interrupted and/or the flow rate can be reduced when the pressure measured by the pressure sensor 35 at the inlet of the first chamber 2 exceeds the venous return pressure measured by the pressure sensor 33 by more than 230 mmHg. The interruption is maintained until the pressure difference from the venous pressure again falls below 200 mmHg. The normal filling operation is only continued then. The pressure difference over the membrane is hereby limited.

The interruption of the switchover of the balancing chamber can take place, for example, in that the fresh water valve 60 arranged between the charging pump 10 and the balancing chamber assembly 11 is closed.

Depending on the embodiment of the method, the valve 43 can be open so that a second flow path is present for leading off the air from the first chamber 2 or the valve 43 can be closed. With a closed valve, the pressure required for building up the pressure difference over the membrane required to displace air over the membrane is reached faster. This can accelerate the filling of membrane filters, in particular large membrane filters.

Provision can be made during the pressure-controlled filling program that no liquid transport takes place from the secondary air separator 18 to the outflow line 22 or 23, i.e. the pumps 20 and 21 are not operated and/or the corresponding valves are closed.

The development of the venous pressure is monitored for as long as the pressure-controlled filling program runs. As long as a change and/or pressure fluctuations of the venous pressure or air is/are observed at the secondary air separator 18, the unit remains in the pressure-controlled filling program such as was described above. A variation of the venous pressure that is, for example, measured via the pressure sensor 33 is here a sign for the air separation over the membrane 50 of the membrane filter 1 from the first chamber 2 into the second chamber 3. Air in the secondary air separator 18 is a sign that air is displaced from the first chamber 2 into the outflow line 7.

If neither pressure changes, for example pressure fluctuations, of the venous pressure nor air are/is detected in the secondary air separator 18, the membrane filter is deemed to be completely filled.

However, the filling program continues to provide a minimum number of switchovers via the dialyzer once a complete treatment has been detected. The minimum number of switchovers is preferably carried out without a pressure control. If air should again be recognized during this time, it is separated via the valve 43 at the secondary air separator.

In the following, the embodiment of the method in accordance with the invention will again be described with further details:

In a first optional step, the membrane filter is filled with normal, i.e. balancing, balancing chamber switchovers, until air has been recognized for so long in the secondary air separator 18 that it has to be assumed that the air separator is idling (for example, max. 3 switchovers with air recognized by the sensor 19). In a possible embodiment of the present invention, this first step can, however, also be dispensed with.

In accordance with the invention, the unit also makes filling switchovers, i.e. non-balancing switchovers, in the pressure-controlled filling program in accordance with the invention, i.e. the charging pump 10 conveys in the direction of the membrane filter 1. The flow is limited to 500 ml/min, for example.

In the filling switchovers, the charging pump conveys at full or reduced power in the direction of the membrane filter. The pressure peaks resulting herefrom at the membrane are first limited by the compliance in the system and by the flow resistances. The excess pressure generated at the dialyzer membrane between the first chamber and the second chamber provides that air passes over the membrane 50 into the second chamber and escapes from there into the environment via the venting 32. This works for so long as the dialyzer membrane is still unwetted, and is therefore air-permeable, at the points at which the air bubbles are located.

If the pressure at the pressure sensor 35 (dialyzer inlet), however, exceeds the venous return pressure by more than 230 mmHg, the switchover is interrupted until the pressure difference from the venous pressure again falls below 200 mmHg. The fresh water valve 60 is only opened again then. The pressure difference over the membrane is hereby limited.

The limitation of the flow and/or pressure over the membrane ensures that no air cushions are enclosed in the fiber bundle that can subsequently no longer be separated.

The valve 43 is continuously open in a first alternative. Air and liquid from the first chamber 2 of the membrane filter 1 can thus additionally reach the drain over this path. How much air escapes over which path depends on the flow resistances of the membrane, on the hydraulics, and on the venting in the second partial circuit.

The valve 43 can, however, also be closed as long as no real dialyzate outlet pressure is present, which could above all accelerate the filling with very large filters.

The development of the venous pressure is monitored for as long as the pressure-controlled filling program runs. As long as a variation of the venous pressure or air is observed at the sensor 19, the unit remains in the pressure-controlled filling program, as in the previous step. A variation of the venous pressure is here a sign that air continues to be displaced over the membrane.

It is ensured by the above monitoring procedures that the membrane is completely wetted at the end of this step (or, if the membrane is e.g. not air-permeable, air no longer escapes over the dialyzate outlet), that is, the membrane filter is filled to the best possible degree (without turning).

A minimum number of switchovers is still carried out over the membrane filter subsequent to the detection of such a filled filter. If air is again recognized during this time, it is separated via the valve 43 via the pressure-controlled filling program.

FIG. 2 shows the progression of the mean dialyzate pressure in a method in accordance with the present invention, i.e. with a pressure control, as a line 71 in comparison with the progression of the mean dialyzate pressure in a method in accordance with the prior art, i.e. without pressure control, that is shown as a line 70. The mean dialyzate pressure is calculated as the mean value of the pressure at the inlet of the chamber 1 (pressure sensor 35) and at the outlet of the chamber 1 (pressure sensor 36).

There is still no real dialyzate pressure applied during the balancing filling phase 74 that is used in both methods since the liquid or air is only displaced in the first partial circuit. In accordance with the present invention, this balancing filling phase 74 can, however, also be dispensed with in an alternative embodiment.

Within the framework of the non-balancing filling phase 75, now pressure controlled, the maximum reached dialyzate pressure initially increases with each balancing chamber switchover. In a first phase 72, the pressure peaks still do not reach the first threshold value 77 so that the pressure control does not intervene. The dialyzate pressure is therefore here solely limited by the compliance of the tubing kit such as was already known from the prior art.

In a second phase 73, the pressure peaks exceed the first threshold value 77, in contrast. If this is recognized by the control, it stops the inflow of dialyzate until the transmembrane pressure and/or the dialyzate pressure is/are again below a second, lower threshold value 78. The normal filling is thereupon resumed again until the first threshold value is again exceeded. A plurality of pressure peaks therefore result per balancing chamber switchover in the embodiment.

As the comparison with the prior art directly shows, work is hereby carried out with a substantially lower maximum dialyzate pressure than in accordance with the prior art. The pressure limitation prevents dialyzate passing from the first chamber into the second chamber during the filling of the first chamber.

A flushing phase 76 in which the pressure drops again follows after the end of the pressure-controlled filling phase 75.

FIG. 3 now shows in detail the pressure developments at the individual pressure sensors during the just described phases of the filling in accordance with the present invention. The individual lines show the following:

80 Pressure at the pressure sensor 35 (pressure at the inlet of the first chamber 2)

81 Pressure at the pressure sensor 36 (pressure at the outlet of the first chamber 2)

82 Pressure at the pressure sensor 33 (pressure in the venous line/in the second chamber 3)

83 Transmembrane pressure

84 Filling state of the first chamber

It can be easily recognized that the pressure 82 in the venous line or in the second chamber 3 fluctuates in the cycle of the balancing chamber switchovers at the start of the pressure-controlled filling phase 75 due to the air displaced over the membrane from the first chamber into the second chamber. After a certain number of balancing chamber switchovers, however, these pressure fluctuations disappear again since the membrane is now soaked and air can no longer be displaced over the membrane. The dialyzate pressure 81 downstream of the first chamber hereby also increases.

The pressure 82 at the blood side can be used in accordance with the invention to detect the complete filling of the membrane filter or the complete soaking of the membrane and/or to control the time sequence and/or the duration of the filling program such as was described in more detail above. The detection of the end of the pressure fluctuations of the pressure 82 is in particular followed by a minimum residual filling phase in which the first chamber continues to be filled.

The transmembrane pressure is limited to an amount by the pressure-controlled filling program, for example of 200 or 250 mbar. A passage of dialyzate into the second chamber is hereby in particular prevented in the minimum residual filling phase in which high transmembrane pressure would occur without such a pressure limitation.

In the embodiment, the pressure-controlled filling program works directly with the transmembrane pressure that is compared with a threshold value. In alternative embodiments, however, the mean dialyzate pressure and/or the pressure at the inlet of the first chamber could also be compared with the threshold value and be limited since the pressure on the dialyzate side and in particular the pressure at the inlet of the first chamber is anyway substantially larger than the pressure on the blood side and therefore substantially determines the transmembrane pressure.

After the filling of the first chamber, the second chamber can be filled in accordance with a method known from the prior art. The filling can take place, for example, by liquid passing over the membrane 50 and/or through the substituate line.

The invention claimed is:

1. A method of filling a membrane filter of a blood treatment system, wherein the blood treatment system has at least one blood treatment machine, a membrane filter, wherein the membrane filter is a hollow fiber membrane filter, having a first and a second chamber that are semipermeably separated by a membrane, and at least one first partial circuit and at least one second partial circuit, wherein the first chamber of the membrane filter is arranged in the first partial circuit and the second chamber of the membrane filter is arranged in the second partial circuit, wherein filling the first chamber of the membrane filter with liquid via the first partial circuit takes place while the second chamber is still filled with air, wherein the first partial circuit is a dialyzate circuit and/or the second partial circuit is an extracorporeal blood circuit, and wherein a pump having a delivery rate is arranged upstream of the membrane filter in the first partial circuit, and wherein the method comprises:

operating the pump to begin filling the first chamber with liquid while the second chamber is still filled with air;

measuring the pressure in the first partial circuit with a first pressure sensor and sending a first pressure signal from the first pressure sensor to a control unit;

evaluating the first pressure signal with the control unit;

controlling the pump for filling the first chamber in dependence on the pressure measured in the first partial circuit and/or on a transmembrane pressure, the controlling of the pump resulting in air present in the first chamber during the filling of the first chamber with liquid being displaced via the membrane into the second chamber and thus into the second partial circuit, controlling the pump with the control unit, to completely stop the pump, as soon as the pressure in the first partial circuit exceeds, and/or the transmembrane pressure exceeds, a first threshold value that is programmed into the control unit, while some air remains present in the first chamber, controlling the pump with the control unit, to start the pump again, from stop, as soon as the pressure in the first partial circuit falls below, and/or the transmembrane pressure falls below, a second threshold value that is programmed into the control unit, wherein an absolute value of the first threshold value is greater than an absolute value of the second threshold value, wherein the starting the pump again from stop again displaces air from the first chamber, via the membrane, into the second partial circuit, repeating the steps of controlling the pump to completely stop the pump and controlling the pump to start the pump again from stop, until the first chamber is filled with the liquid and no air is again displaced from the first chamber, via the membrane, into the second partial circuit, while the second partial circuit is not yet filled with liquid, and filling the second chamber with liquid after the first chamber is filled with liquid.

2. The method in accordance with claim 1, wherein a volume flow used for filling and generated by the pump and/or the time development and/or the duration of the filling by the pump is controlled in dependence on the pressure measured in the first and/or second partial circuit(s).

3. The method in accordance with claim 1, wherein a pressure in the first partial circuit and/or a transmembrane pressure over the membrane of the membrane filter is determined and the controlling of the pump for filling the first chamber of the membrane filter via the first partial circuit takes place in dependence on the pressure in the first partial circuit and/or on the transmembrane pressure.

4. The method in accordance with claim 1, wherein the first threshold value amounts to at least 50 mbar.

5. The method in accordance with claim 1, wherein the second threshold value amounts to at least 50 mbar.

6. The method in accordance with claim 1, wherein the pump is controlled such that an excess pressure arises in the first chamber of the membrane filter, and the excess pressure amounts to at least 50 mbar.

7. The method in accordance with claim 1, wherein the pump for filling the first chamber of the membrane filter is controlled in a volume-controlled manner, with the volume-controlled control being stopped or the volume flow being reduced as soon as the pressure in the first partial circuit and/or the transmembrane pressure exceeds/exceed the first threshold value, and/or with the volume-controlled control being resumed or the volume flow being increased as soon as the pressure in the first partial circuit and/or the transmembrane pressure falls below the second threshold value.

8. The method in accordance with claim 1, wherein the first chamber of the membrane filter is filled with a pulsatile volume flow by which pressure peaks are generated in the first chamber of the membrane filter, and the pump cooperates with a balancing chamber assembly that has liquid applied by the pump and that runs switching over processes that result in the pulsatile volume flow.

9. The method in accordance with claim 1, wherein no liquid is drained from the system, at least at times, during the pressure-controlled filling of the first chamber of the membrane filter and/or wherein a pump arranged downstream of the membrane filter in the first dialyzate circuit is not operated, at least at times, during the filling of the first chamber of the membrane filter.

10. The method in accordance with claim 1, wherein a pressure in the second partial circuit is measured and the filling of the first chamber of the membrane filter takes place via the first partial circuit in dependence on the pressure in the second partial circuit, with dynamic and/or static pressure changes in the second partial circuit being detected and/or monitored.

11. The method in accordance with claim 1, wherein the filling is continued for so long as pressure fluctuations are detected in the second partial circuit and/or air is detected in a secondary air separator of the first partial circuit, with a minimum residual filling phase still being carried out once pressure fluctuations and/or air are no longer detected, with the minimum residual filling phase comprising a predefined pump volume, a predefined time, a predefined number of pump beats, and/or a predefined number of balancing chamber switchovers.

12. The method in accordance with claim 11, wherein a minimum residual filling phase is carried out once pressure fluctuations are no longer detected and the minimum residual filling phase comprises pumping a predefined pump volume, pumping for a predefined time, pumping for a predefined number of pump beats, and/or pumping for a predefined number of balancing chamber switchovers.

13. The method in accordance with claim 1, wherein the second partial circuit is in fluid communication with atmosphere during the filling of the first chamber of the membrane filter via the first partial circuit.

14. The method in accordance with claim 1, wherein the second partial circuit is in fluid communication with atmosphere during the filling of the first chamber of the membrane filter via an element that generates a pressure drop.

15. The method in accordance with claim 1, wherein liquid and/or air is/are displaced from the first chamber into a secondary air separator during the filling of the first chamber of the membrane filter via the first partial circuit, the secondary air separator being arranged in the first partial circuit downstream of the membrane filter.

16. The method in accordance with claim 15, wherein the secondary air separator is not connected to a liquid outflow of the blood treatment system at least at times.

17. The method in accordance with claim 1, wherein the first partial circuit is not filled in a balancing manner, at least at times, during the pressure-controlled filling, with the filling of the first chamber of the membrane filter via the first partial circuit starting without a balancing phase and/or taking place in a non-balancing manner at least up to a detection of a filling.

18. The method in accordance with claim 1, wherein, after the second chamber is filled with liquid, pumping blood in the second partial circuit to the second chamber.

19. A blood treatment machine to which a membrane filter is coupled, the membrane filter being a hollow fiber membrane filter having a first chamber and a second chamber that are semipermeably separated from one another by a membrane, said blood treatment machine comprising:

at least one first pump actuator of a first pump having a delivery rate for pumping liquid in a first partial circuit and at least one second pump actuator of a second pump for pumping liquid in a second partial circuit, wherein the first chamber of the membrane filter is arranged in the first partial circuit, the second chamber of the membrane filter is arranged in the second partial circuit, and the first pump is arranged upstream of the membrane filter in the first partial circuit;

at least one first pressure sensor for measuring a pressure in the first partial circuit; and a control unit that evaluates signals of the at least one first pressure sensor and controls the at least one first pump actuator based on the signals evaluated, wherein the control unit is programmed with a filling program that carries out a control of the first pump actuator for filling the first chamber of the membrane filter via the first partial circuit, in dependence on the pressure measured in the first partial circuit and/or a measured transmembrane pressure, such that air present in the first chamber during the filling of the first chamber of the membrane filter with liquid is displaced via the membrane into the second chamber of the membrane filter and thus into the second partial circuit, the first pump is completely stopped as soon as the pressure in the first partial circuit and/or the transmembrane pressure exceeds/exceed a first threshold value that is programmed into the control unit, while some air remains present in the first chamber, the first pump is started again from stop as soon as the pressure in the first partial circuit and/or the transmembrane pressure falls/fall below a second threshold value that is programmed into the control unit, wherein an absolute value of the first threshold value is greater than an absolute value of the second threshold value, upon the controlling the pump with the control unit, to start the pump again from stop, air is again displaced from the first chamber, via the membrane, into the second partial circuit, the steps of controlling the pump to completely stop the pump and controlling the pump to start the pump again from stop, are repeated until the first chamber is filled with the liquid and no air is again displaced from the first chamber, via the membrane, into the second partial circuit, while the second partial circuit is not yet filled with liquid, and subsequently, after the filling of the first chamber with liquid, the second chamber is filled with liquid.

20. The blood treatment machine in accordance with claim 19, wherein the control unit controls one or more pump actuators and/or one or more valve actuators that actuate valves of the first and/or second partial circuit(s) for the carrying out of the filling program, and/or wherein the working through of the filling program, takes place automatically by the control unit.

* * * * *